United States Patent
Tanjavur (10) Patent No.: US 12,383,715 B1
(45) Date of Patent: Aug. 12, 2025

(54) VASCULAR ACCESS SHEATH AND DILATOR ASSEMBLY

(71) Applicant: Vijayakumar Tanjavur, Ft. Myers, FL (US)

(72) Inventor: Vijayakumar Tanjavur, Ft. Myers, FL (US)

(*) Notice: Subject to any disclaimer, the term of this patent is extended or adjusted under 35 U.S.C. 154(b) by 0 days.

(21) Appl. No.: 18/904,918

(22) Filed: Oct. 2, 2024

(51) Int. Cl.
  *A61M 29/02* (2006.01)
  *A61M 25/00* (2006.01)
  *A61M 25/06* (2006.01)

(52) U.S. Cl.
  CPC ........ *A61M 29/02* (2013.01); *A61M 25/0043* (2013.01); *A61M 25/0662* (2013.01); *A61M 2025/0687* (2013.01); *A61M 2029/025* (2013.01); *A61M 2205/32* (2013.01); *A61M 2205/582* (2013.01); *A61M 2205/583* (2013.01); *A61M 2205/6036* (2013.01); *A61M 2205/6045* (2013.01)

(58) Field of Classification Search
  CPC .............. A61M 29/02; A61M 25/0043; A61M 25/0662; A61M 2025/0687; A61M 2029/025; A61M 2205/32; A61M 2205/582; A61M 2205/583; A61M 2205/6036; A61M 2205/6045
  See application file for complete search history.

(56) References Cited

U.S. PATENT DOCUMENTS

| | | | |
|---|---|---|---|
| 4,033,331 A | 7/1977 | Guss et al. | |
| 4,774,949 A | 10/1988 | Fogarty | |
| 5,873,865 A | 2/1999 | Horzewski et al. | |
| 5,916,194 A | 6/1999 | Jacobsen et al. | |
| 7,182,756 B2 | 2/2007 | Saeed et al. | |
| 7,276,064 B2 | 10/2007 | Paul et al. | |
| 7,695,508 B2 | 4/2010 | Der Leest et al. | |
| 7,842,041 B2 | 11/2010 | Liu et al. | |
| 8,636,715 B2 | 1/2014 | Patel | |
| 8,696,620 B2 | 4/2014 | Tegg | |
| 10,864,041 B2 | 12/2020 | Urbanski et al. | |
| 2001/0034514 A1* | 10/2001 | Parker | A61M 25/005 604/525 |
| 2009/0105711 A1* | 4/2009 | Mitchell | A61B 17/885 606/92 |
| 2017/0333674 A1 | 11/2017 | Walzman | |
| 2018/0200490 A1* | 7/2018 | Gianotti | A61M 29/00 |
| 2019/0380563 A1* | 12/2019 | Sanghvi | A61M 25/0662 |

* cited by examiner

*Primary Examiner* — Richard G Louis (74) *Attorney, Agent, or Firm* — Bold IP, PLLC; Binita J. Singh (57) ABSTRACT

The invention provides an improved vascular sheath and dilator assembly designed to enhance maneuverability, procedural accuracy, and safety during vascular access. The assembly includes a vascular sheath with a side port and a dilator featuring a closed distal end and a deflecting portion within its lumen. This deflecting portion smoothly redirects a guidewire towards a side port in the dilator aligned with the side port of the vascular sheath when the dilator is properly positioned within the vascular sheath, thus facilitating precise navigation of the guidewire into side vessels of a vascular structure. The assembly also incorporates visual markers on both the vascular sheath and the dilator to ensure accurate alignment of the side ports. These features collectively improve overall efficacy and safety in vascular procedures.

18 Claims, 8 Drawing Sheets

VASCULAR ACCESS SHEATH AND DILATOR ASSEMBLY

FIELD OF THE DISCLOSURE

The present invention relates to medical devices, specifically to a vascular access sheath and dilator assembly designed to facilitate vascular access procedures.

BACKGROUND

Vascular access is critical for numerous medical procedures, such as diagnostic angiography, angioplasty, and the insertion of various intravascular devices. Traditional vascular sheaths and dilators are commonly used to create and maintain access to blood vessels. However, current devices lack features that facilitate precise navigation and alignment at the point of entry, which is necessary in certain circumstances.

There is an increasing demand for antegrade access to the femoral artery for ipsilateral lower limb arterial interventions due to a rise in patients with complex vascular histories. Specifically, the prevalence of patients who have undergone previous aortic bypass grafts or endovascular aortic stent grafts, coupled with progressive peripheral artery disease (PAD), is on the rise. This trend highlights a critical shift in the approach to accessing the femoral artery for therapeutic procedures.

Traditionally, the initial approach for lower limb arterial interventions has involved obtaining access retrograde from the contralateral common femoral artery. This method relies on crossing over to the diseased limb through the aortic bifurcation to facilitate intervention. However, this technique becomes unfeasible in patients with previous endovascular aortic stent grafts or those with a history of open aortic surgery involving Dacron bypass grafts. In such cases, antegrade access to the femoral artery on the same side as the disease (ipsilateral approach) becomes a necessary alternative.

Antegrade access to the femoral artery, while essential for certain clinical scenarios, presents several technical challenges that make the procedure more complex compared to traditional retrograde approaches: 1) The common femoral artery often has a short segment available for catheter manipulation, which can restrict maneuverability. The limited length of the artery complicates the ability to advance and position instruments effectively 2) During antegrade access, there is a high chance of the initial guidewire entering the profunda femoral artery (also known as the deep femoral artery) or its branches instead of the target superficial femoral artery (also known as femoral artery). Redirecting the guidewire back into the femoral artery is a delicate task that can be unreliable and may result in loss of access or increased procedural time. 3) The femoral artery often exhibits acute angulation relative to the entry point of the access needle. This anatomical challenge makes it difficult to achieve a straight and stable pathway for the guidewire and catheter, increasing the risk of procedural complications. 4) The presence of atherosclerotic disease at the origin of the femoral artery can cause stenosis or occlusion, which obstructs the passage of the guidewire and complicates access. This can lead to difficulties in gaining initial access and increases the risk of procedural failure.

Recent advancements in interventional techniques and technologies have been developed to address these challenges. There are enhanced imaging modalities, such as intravascular ultrasound (IVUS) and optical coherence tomography (OCT), which can assist in visualizing vascular anatomy and guidewire placement. Additionally, there is also an increased focus on training and simulation for antegrade access techniques which allows practitioners to better prepare for the complexities of these procedures, reducing the likelihood of errors and improving overall outcomes. Despite these successes, challenges remain, such as high costs and limited availability of advanced imaging technologies, the need for advanced skills to effectively use new tools and technologies, persistent difficulties in accessing complex anatomical structures, and other challenges. There are double-lumen catheters that offer guidewire deflection features, but these catheters are not intended for initial access and are not suitable as a vascular sheath for achieving entry into the superficial femoral artery.

Accordingly, there is a need for a vascular sheath with a simple, reliable, and easy method for gaining access to the femoral artery via an antegrade approach. Additionally, such a sheath should not only facilitate initial arterial access but also be designed to integrate seamlessly with other guiding catheters. These guiding catheters should be capable of redirecting the guidewire 180 degrees in the opposite direction, making it suitable for a range of applications including Arteriovenous (AV) fistula imaging and interventions. This dual functionality is essential for improving the effectiveness of procedures that require precise access and navigation of complex vascular anatomies.

SUMMARY

The present invention provides for a vascular access sheath and dilator assembly designed to facilitate vascular access procedures. According to one embodiment, one or more embodiments are provided with a vascular access sheath and a dilator that are each engineered with side ports designed to align with each other when the dilator is inserted into the vascular sheath. The vascular sheath and dilator assembly comprises the vascular sheath that includes a tubular structure with a proximal end, a distal end, and a lumen extending longitudinally between the two ends. The vascular sheath also has a side port located on the side of the tubular structure, which extends into the lumen. The assembly further includes the dilator configured for insertion into the lumen of the vascular sheath. The dilator consists of a cylindrical device with a proximal end, a distal end, and a lumen extending longitudinally along its length. The dilator also includes a side port positioned on the side of the cylindrical device, which aligns with the side port of the vascular sheath when the dilator is fully inserted. Additionally, the distal end of the dilator is closed to prevent a guidewire from exiting through the distal end.

The dilator also includes a deflecting portion in the lumen to assist with navigating a guidewire through the side ports of the dilator and the vascular access sheath. A radio opaque marker is also integrated on the vascular sheath to indicate the location of the side port. Markers, positioned externally on both the vascular sheath and dilator, allow proper alignment of the side ports.

This invention aims to enhance the efficiency and safety of vascular access procedures by providing improved device alignment and navigation capabilities. This is both advantageous to the provider, support staff, and most importantly increases safety for the patient.

Other aspects and advantages of the invention will be apparent from the following description and the appended claims.

BRIEF DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

DETAILED DESCRIPTION

In the Summary above and in this Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, among others, are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose lower limit is the first number and whose upper limit is the second number. For example, 25 to 100 mm means a range whose lower limit is 25 mm and upper limit is 100 mm.

Certain terminology and derivations thereof may be used in the following description for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "coupled to" as used herein may mean a direct or indirect connection via one or more components.

The present disclosure is generally drawn to one or more embodiments for a vascular sheath and dilator assembly designed to facilitate vascular access procedures. Vascular access is a critical component in various medical procedures, including catheterization, angiography, and endovascular surgeries. Conventional vascular sheaths and dilators, an example of which is shown in FIGS. 1 to 4, typically lack mechanisms for accessing collateral or side vessels off the main vessel, leading to inefficiencies and potential complications during procedures. The present invention addresses these issues by providing a vascular sheath and dilator with side ports that align when assembled, ensuring efficient procedural precision. The present invention includes a vascular sheath with a side port, a dilator with a side port and a lumen with a deflecting portion, and a radio-opaque marker to indicate the location of the side port on the vascular sheath. Additionally, a marker on the vascular sheath and a marker on the dilator are designed to align the side ports on both components when the markers are matched up during the insertion of the dilator into the vascular sheath. This invention aims to enhance the efficiency and safety of vascular access procedures by providing improved device alignment and navigation capabilities. The embodiments provided herein may be utilized for multiple purposes, including but not limited to improving the precision and safety of vascular access. Further details are provided below with reference to the Figures.

Turning to the figures, FIGS. 1 to 4 depict a prior art vascular sheath and dilator assembly 500 which consists of a vascular sheath 510 and a corresponding dilator 520, both designed for basic vascular access procedures. The vascular sheath 510 is a tubular structure comprising a proximal end 512 and a distal end 514, with a lumen 516 extending longitudinally between the two ends. The lumen 516 is configured to receive the dilator 520 during insertion into a vascular structure. The distal end 514 of the sheath 510 is typically tapered to facilitate smooth entry into a vessel, minimizing trauma to a vessel wall.

The prior art dilator 520, intended to be inserted into the lumen 516 of the vascular sheath 510, includes a proximal end 522 and a distal end 524, with a lumen 526 extending through its length. The distal end 524 of the dilator 520 is designed to be open, allowing for the insertion of a guidewire 600 through the open distal end 524 into a vascular structure during the procedure. The open distal end 524 aids in guiding the vascular sheath 510 into position within the vascular system by permitting the passage of the guidewire 600 through the dilator 520 and into the targeted vessel.

The assembly 500 is primarily designed to provide a conduit for introducing guidewires into the vascular system. While it ensures structural integrity and facilitates basic vascular access, this prior art design lacks additional features that would enable maneuverability within the sheath. The prior art vascular sheath and dilator assembly 500 presents certain limitations, particularly in procedures where access to a side vessel branching off a main vessel is required. In such scenarios, the physician must rely heavily on manual manipulation of the guidewire through the open distal end 524 of the dilator 520 to navigate the guidewire 600 from the main vessel into the side vessel.

Since the prior art assembly 500 lacks any specialized features to aid in precise positioning, the physician is compelled to use a trial-and-error approach. This process often involves repeatedly advancing and retracting the guidewire 600, as well as rotating or repositioning the entire assembly 500, to locate the opening of the side vessel. Without visual or positional cues provided by the assembly 500, the physician must depend on tactile feedback and imaging techniques, which can be time-consuming and less accurate.

Now referring to FIGS. 5 to 8, one or more embodiments of a vascular sheath and dilator assembly 100 of the present invention addresses the limitations of prior art devices. The vascular sheath and dilator assembly 100 includes a vascular sheath 110 and a dilator 120. The term "vascular sheath and dilator assembly" may also be referred to as "assembly" and is intended to encompass all components described herein, including the vascular sheath, dilator, and any associated parts or features, regardless of specific terminology used throughout this document.

The assembly 100 is specifically engineered to facilitate the precise navigation of a guidewire 600 into a side vessel branching from a main vessel, thereby improving procedural accuracy, efficiency, and safety.

The vascular sheath 110 is a tubular structure comprising a proximal end 112, a distal end 114, and a lumen 116 extending longitudinally therebetween. The lumen 116 is configured to receive the dilator 120 for the purpose of facilitating vascular access procedures. As used herein, the term "vascular sheath" may also be referred to as "vascular access sheath," "introducer sheath," "access sheath," or simply "sheath," and all such terms are intended to refer to the same component throughout this document.

The vascular sheath 110 further includes a side port 118, strategically positioned between the proximal end 112 and the distal end 114. This side port 118 is an opening in a side of the vascular sheath 110, specifically engineered to allow for controlled access into a side branch or vessel. In other words, the position of the side port 118 is optimized to enhance procedural control such as accessing a side vessel during vascular access procedures.

Additionally, the vascular sheath 110 is provided with a radio-opaque marker 140. The radio-opaque marker 140 is located proximal to the side port 118 of the vascular sheath. This alignment allows the practitioner to accurately determine the position of the side port 118 using imaging techniques to position the side port 118 at a side vessel, thereby improving the safety and precision of the procedure. The radio-opaque marker 140 ensures that the side port 118 can be reliably located in relation to anatomical structures during insertion and positioning within the vascular system.

The dilator 120 is a cylindrical device designed for insertion into the lumen 116 of the vascular sheath 110. The dilator 120 comprises a proximal end 122, a distal end 124, and a lumen 126 extending longitudinally between these ends. The lumen 126 is dimensioned to accommodate the passage of guidewires, fluids, or other medical instruments as required during the procedure. The dilator 120 of the present invention features a closed distal end 124, contrasting with the open distal end 524 of the prior art lumen 526 in FIGS. 1 to 4.

The dilator 120 includes a side port 128 located near the distal end 124. The side port 128 is also an opening in a side of the dilator 120 positioned to align with the side port 118 of the vascular sheath 110 when the dilator 120 is fully inserted into the sheath 110. This alignment is facilitated by the design of the dilator 120, which includes a deflecting portion 127 within the lumen 126 near the side port 128. This deflecting portion 127 is specifically engineered to guide and redirect the guidewire 600 laterally through the side port 128 and into the aligned side port 118 of the vascular sheath 110.

Figure 7:
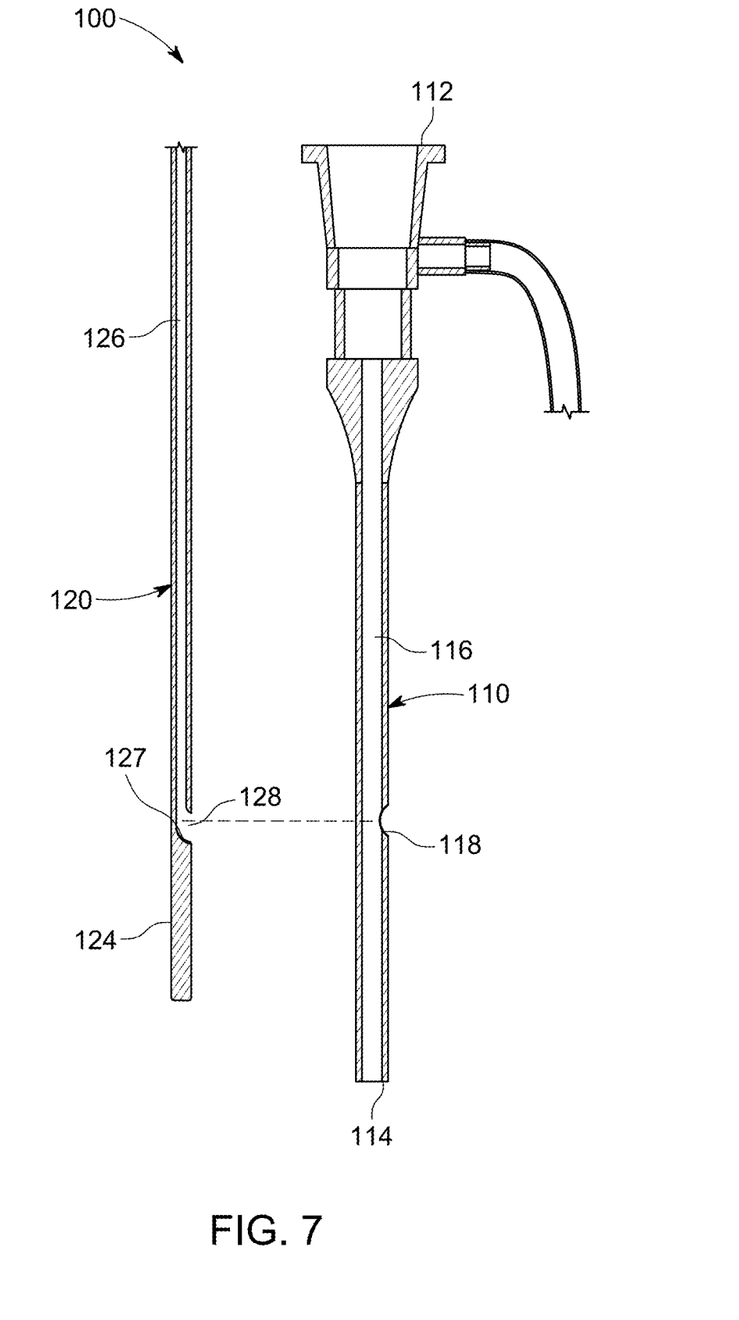
FIG. 7 is a pictorial illustration of a cross-sectional view of the vascular sheath and dilator along a center line of each in accordance with an illustrative embodiment.
Figure 8:
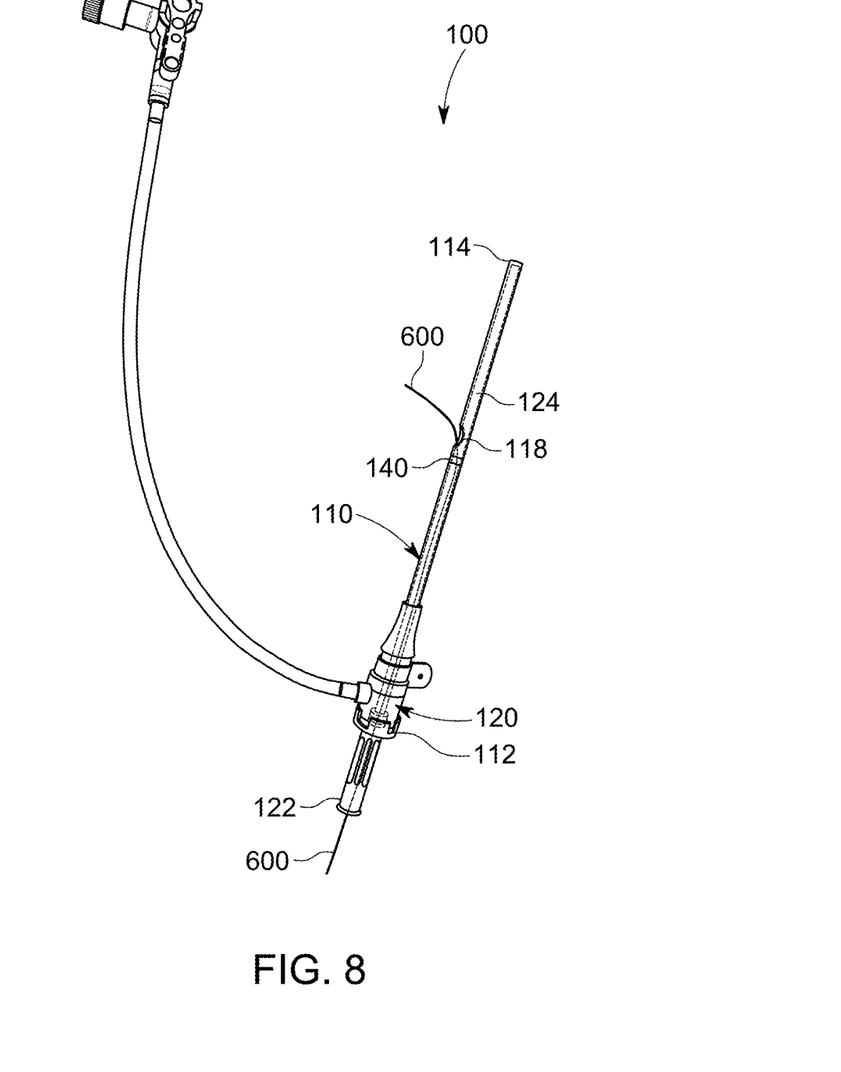
FIG. 8 is a pictorial illustration of a guidewire positioned through the dilator positioned within the vascular sheath in accordance with an illustrative embodiment.

The deflecting portion 127 within the lumen 126 of the dilator 120 is a critical feature of the present invention, designed to facilitate the smooth and controlled deflection of the guidewire 600 toward the side ports 128 and 118. The closed distal end 124 design enhances the structural integrity of the dilator 120 and prevents the guidewire 600 from inadvertently exiting the distal end 124, ensuring that the guidewire 600 is directed precisely through the side port 128 for accurate access to side vessels. The deflecting portion 127 is integrally formed within the lumen 126 of the dilator 120, situated proximally adjacent to the side port 128. This deflecting portion 127 is characterized by a gently sloping, smooth surface that is specifically contoured to guide the guidewire 600 from a central axis of the lumen 126 toward the side port 128 without causing any abrupt changes in direction or excessive friction.

The deflecting portion 127 is engineered with a gradual, curved profile. This smooth curvature ensures that as the guidewire 600 advances through the lumen 126, it encounters a seamless transition as it is redirected laterally. The absence of sharp edges or abrupt angles minimizes the risk of kinking or damaging the guidewire 600, promoting a steady and controlled movement through the lumen. The smooth surface of the deflecting portion 127 is further optimized to reduce resistance, allowing the guidewire 600 to glide effortlessly along its contour. As the guidewire 600 reaches the deflecting portion 127, the gradual slope gently nudges it toward the side port 128, facilitating a fluid and uninterrupted passage out of the side port 128 and into the aligned side port 118 of the vascular sheath 110.

This design of the deflection portion 128 ensures that the guidewire 600 maintains its integrity and precise trajectory as it transitions from the dilator 120 into the side vessel. The deflecting portion 127 thus plays a vital role in enhancing the overall performance of the assembly, providing a reliable and efficient means of directing the guidewire 600 with minimal operator effort and maximum procedural accuracy.

Figure 1:
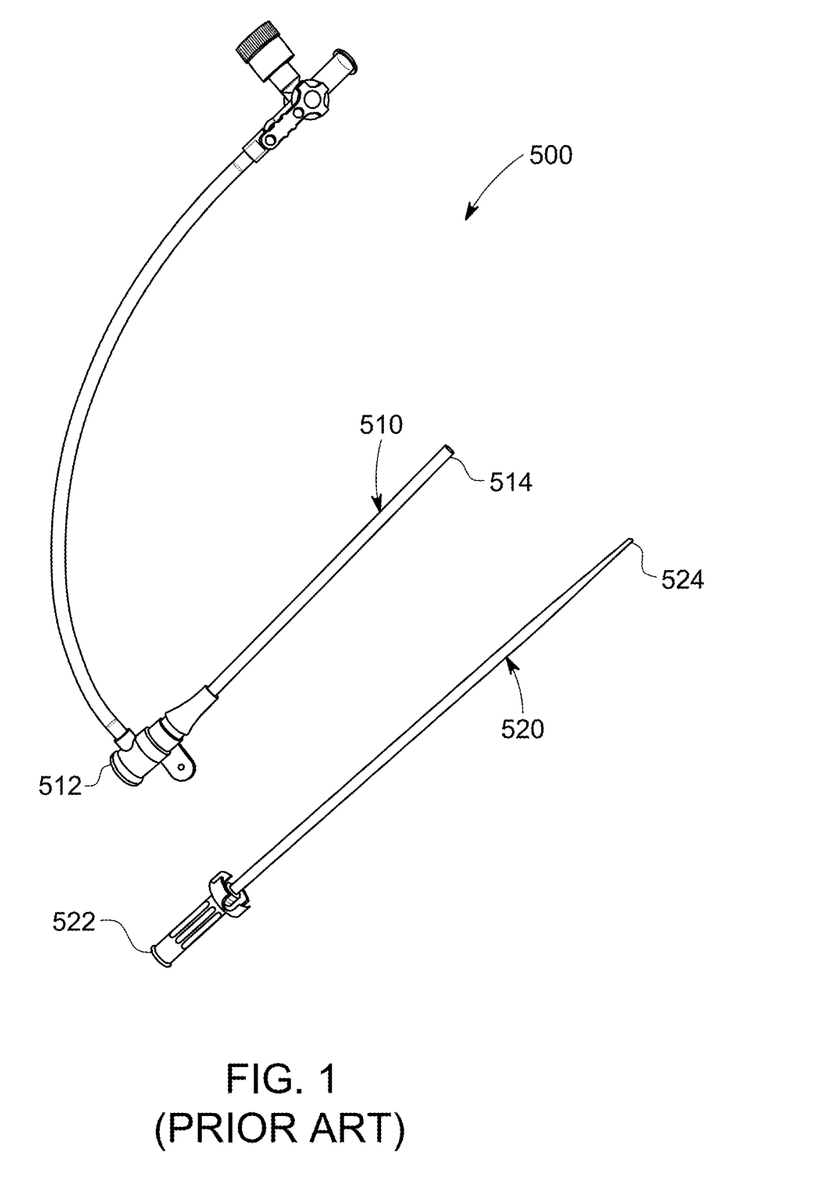
FIG. 1 is a pictorial illustration of a prior art vascular sheath and dilator.
Figure 2:
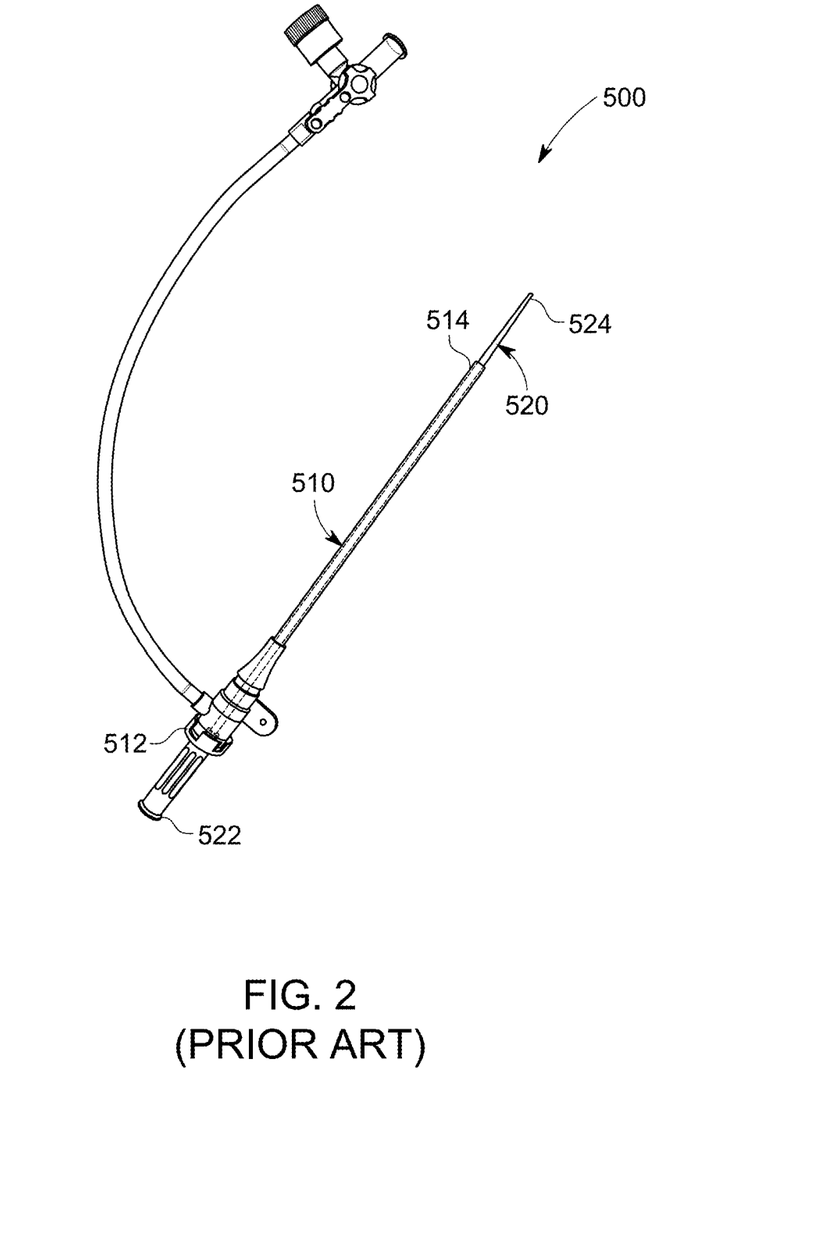
FIG. 2 is a pictorial illustration of the prior art vascular sheath and dilator in cooperation with each other.
Figure 3:
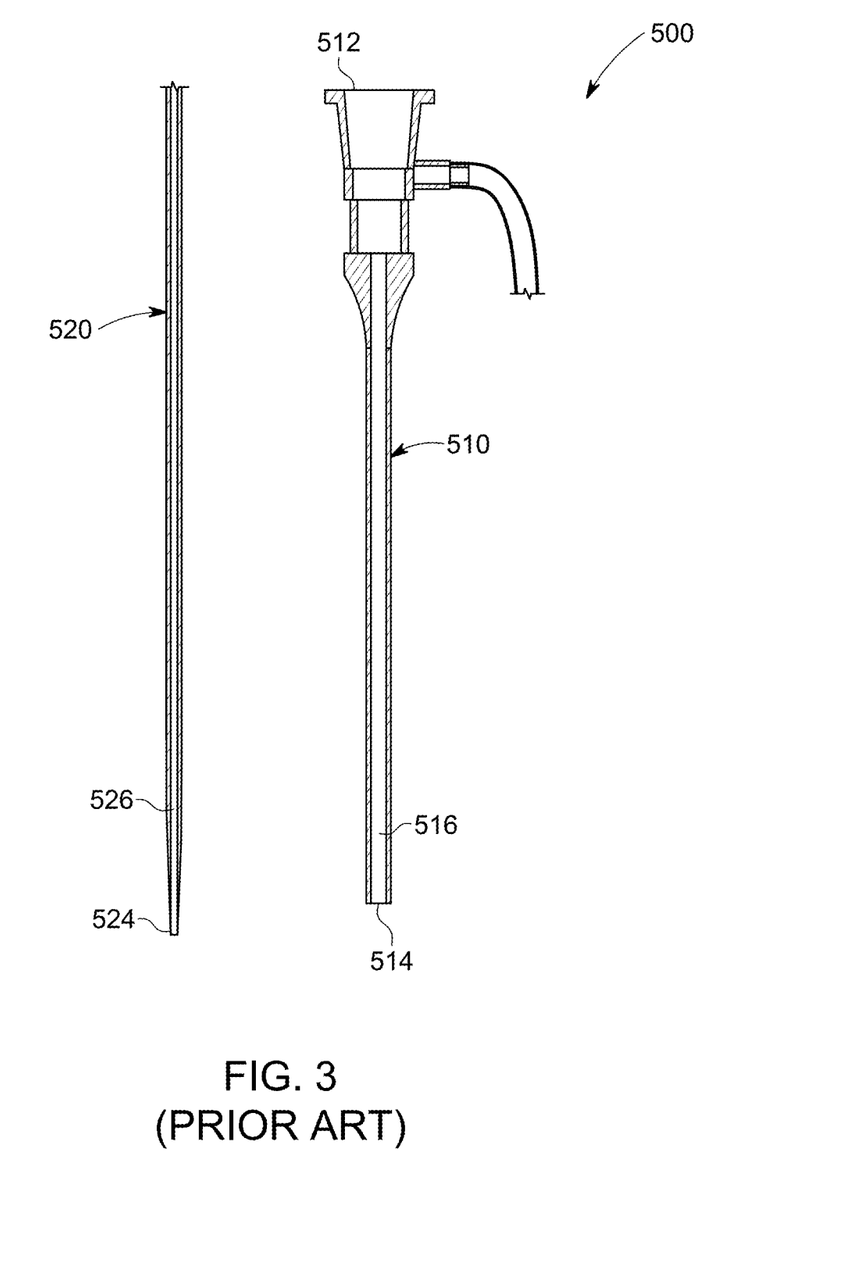
FIG. 3 is a pictorial illustration of a cross-sectional view of the prior art vascular sheath and the dilator along a center line of each.
Figure 4:
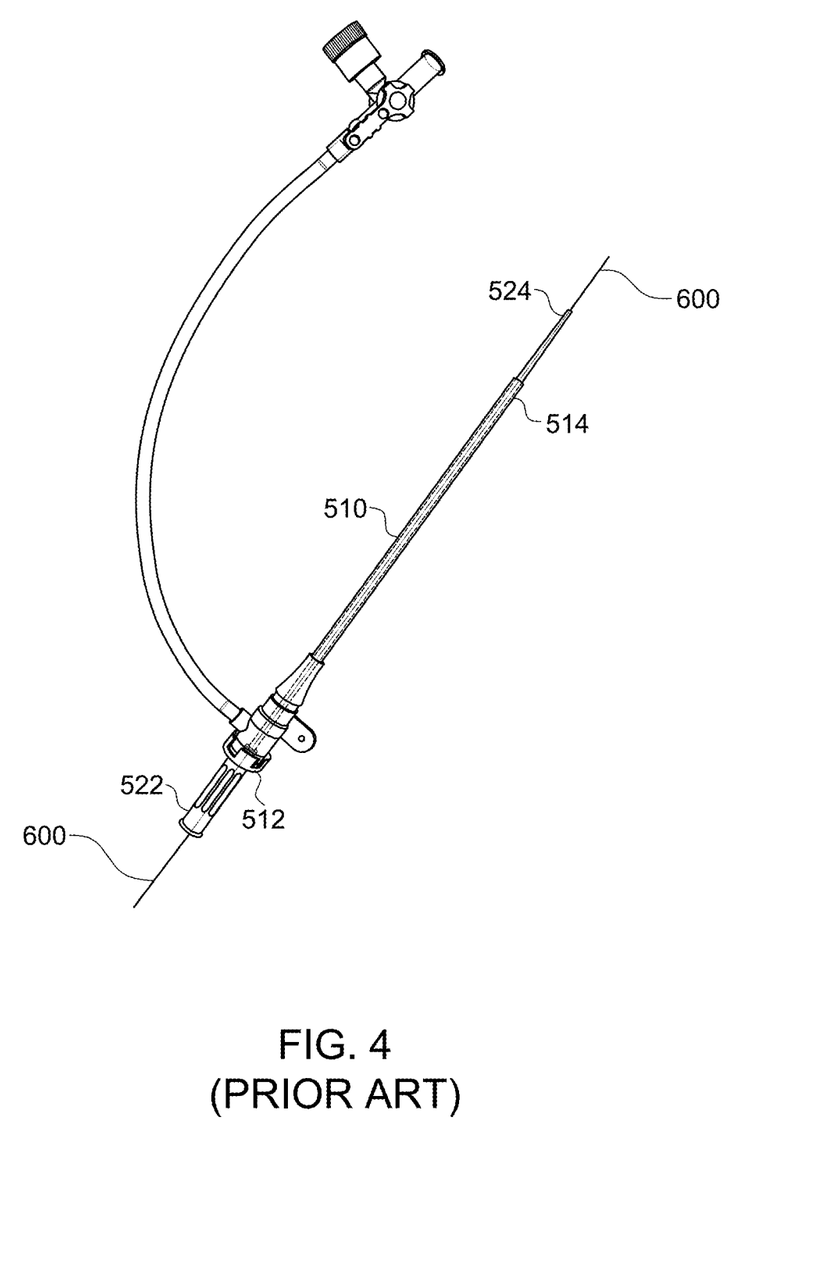
FIG. 4 a pictorial illustration of a guidewire positioned through the prior art dilator positioned within the vascular sheath.
Figure 5:
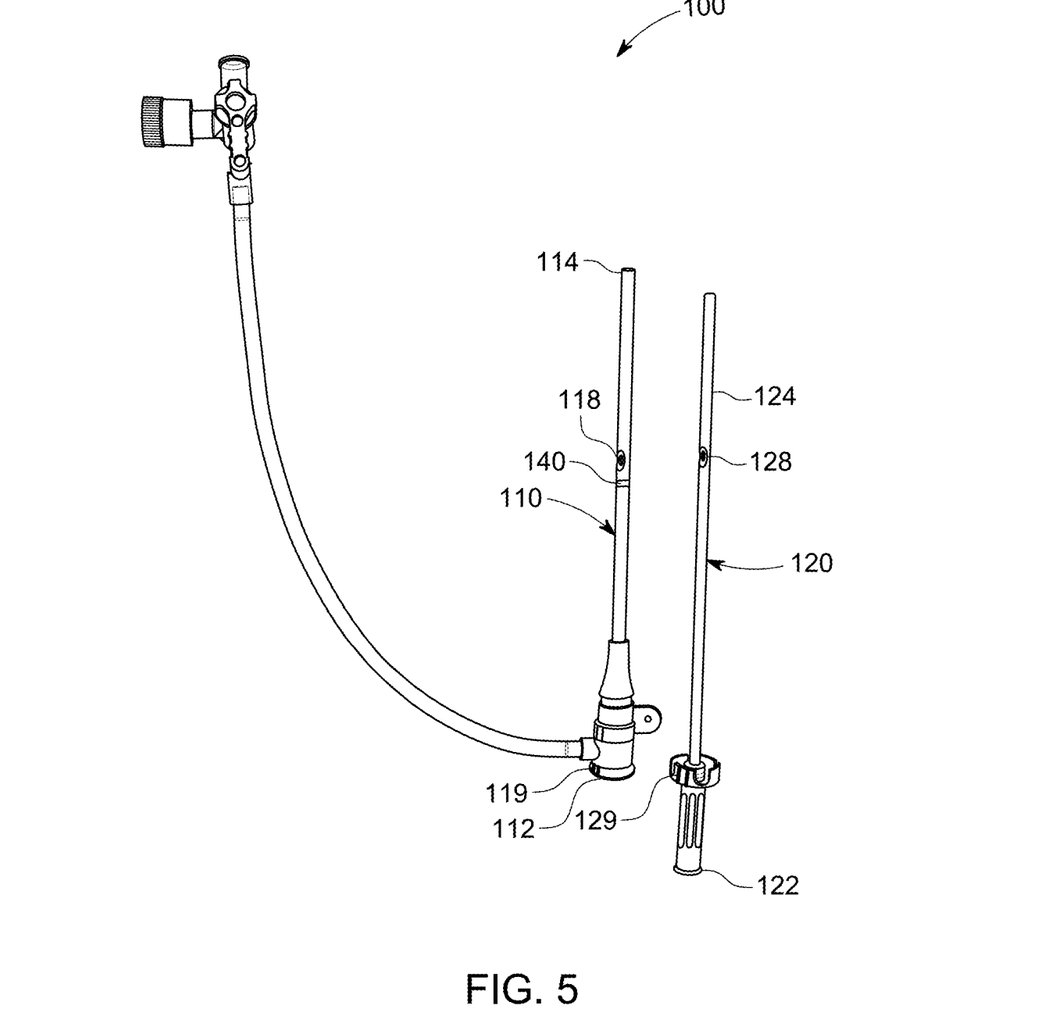
FIG. 5 is a pictorial illustration of a perspective view of a vascular sheath and a dilator assembly in accordance with an illustrative embodiment of the present invention.
Figure 6:
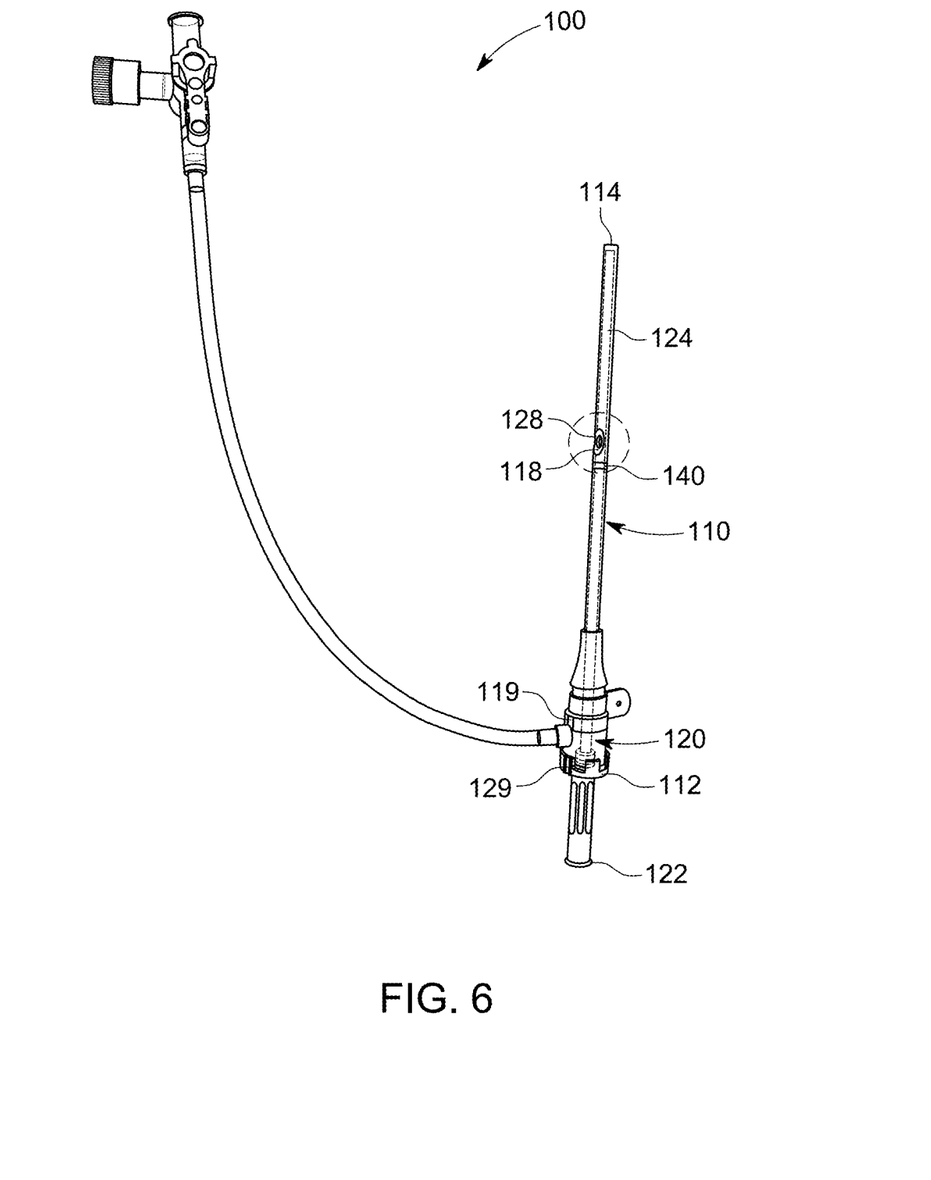
FIG. 6 is a pictorial illustration of the vascular sheath and dilator assembly of FIG. 5 in cooperation with each other in accordance with an illustrative embodiment.

Furthermore, the vascular sheath 110 and the dilator 120 are equipped with a first marker 119 and a second marker 129, respectively. The dilator 120 is equipped with the second marker 129 at its proximal end 122. The second marker 129 is configured to correspond with the first marker 119 on the vascular sheath 110 when the dilator 120 is properly aligned within the vascular sheath 110.

These markers 119, 129 can be visual markers, such as lines, arrows, or color indicators, which provide a clear and immediate visual confirmation of proper alignment. Alternatively, the markers 119, 129 can be tactile markers, such as raised surfaces, ridges, or notches, allowing the user to feel when the dilator and the sheath are properly aligned, which is particularly useful for users relying on sensory feedback during insertion. In another configuration, the markers 119 and 129 could take the form of mechanical features, such as indentations or protrusions. Once the dilator 120 is inserted into the vascular sheath 110, proper alignment occurs when these mechanical features are fitted together. This ensures that the side ports 118 and 128 are correctly aligned, which is essential for accessing a side vessel. If the features are not properly aligned, the side ports will remain misaligned.

This alignment of side ports 118, 128 allows for accurate control during a procedure, guiding the guidewire 600 into a side vessel while minimizing the risk of misalignment. By incorporating such markers 119, 129—whether visual, tactile, or mechanical—the device ensures reliable orientation of the dilator 120 within the vascular sheath 110, enhancing both ease of use and procedural safety.

The combination of these features—the side ports 118 and 128, the markers 119 and 129, and the deflecting portion 127—provides a robust and reliable system for vascular access, enhancing both the accuracy and safety of procedures by allowing for controlled and precise guidewire placement and positioning.

During a vascular access procedure, the physician advances the guidewire 600 through the lumen 126 of the dilator 120. As the guidewire 600 approaches the distal end 124, it encounters the deflecting portion 127. The deflecting portion 127 smoothly redirects the guidewire 600 toward the side port 128 in the dilator 120. Upon exiting the side port 128, the guidewire 600 passes through the aligned side port 118 in the vascular sheath 110 and is thereby directed into the side vessel branching from the main vessel.

This guided deflection of the guidewire 600 provides several key advantages. The alignment of the side ports 118 and 128, combined with the action of the deflecting portion 127, ensures that the guidewire 600 is accurately directed into the side vessel. This eliminates the need for trial-and-error manipulation, which is commonly required with prior art assemblies that lack such features.

The ability to guide the guidewire 600 consistently and accurately into the side vessel on the first attempt significantly reduces the overall time required for the procedure. The physician can efficiently position the guidewire 600 without repeated adjustments, thus streamlining the procedure.

The controlled deflection of the guidewire 600 into the side vessel reduces the need for extensive manipulation, thereby minimizing the risk of trauma to the vessel walls. This is particularly advantageous in procedures involving delicate or tortuous vascular anatomy, where the risk of injury is higher.

The aligned side ports 118 and 128 also facilitate the targeted delivery of fluids or contrast agents directly into the side vessel. This capability is critical in procedures requiring precise administration of therapeutic agents or imaging contrast, further enhancing the procedural outcome.

The vascular sheath and dilator assembly 100 of the present invention provides a superior solution to the limitations of prior art devices. By incorporating side ports 118 and 128, along with the deflecting portion 127, the invention allows for precise, controlled access to side vessels, thereby improving procedural accuracy, reducing time, and minimizing the risk of complications. The enhanced functionality of this assembly represents a significant advancement in the field of vascular access, offering substantial benefits to both physicians and patients. Many additional advantages and uses are offered by the one or more systems described herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. A vascular sheath and dilator assembly comprising:
    a vascular sheath including:
        a tubular structure having a proximal end, a distal end, and a lumen extending longitudinally therebetween;
        a side port located on a side of the tubular structure and extending into the lumen of the tubular structure;
    a dilator configured for insertion into the lumen of the vascular sheath, the dilator including:
        a cylindrical device having a proximal end, a distal end, and a lumen extending longitudinally therebetween;
        a side port located on a side of the cylindrical device extending into the lumen of the cylindrical device and aligned with the side port of the vascular sheath when the dilator is fully inserted into the sheath;
        a closed distal end designed to prevent a guidewire from exiting the distal end of the dilator;
    wherein vascular access into a side vessel branching off a main vessel using the vascular sheath and dilator assembly comprises:
        inserting the vascular sheath into a vascular vessel and aligning the side port of the vascular sheath with a side vessel branching from a main vessel;
        inserting the dilator into the lumen of the vascular sheath and aligning the side port of the dilator with the side port of the vascular sheath;
        advancing a guidewire through the lumen of the dilator; and
        guiding the guidewire laterally through the side port of the dilator and into the aligned side port of the vascular sheath, thereby directing the guidewire into a side vessel branching from a main vessel.

2. The assembly of claim 1, wherein the vascular sheath includes a radio-opaque marker positioned proximal to the side port of the vascular sheath.

3. The assembly of claim 1, wherein the dilator further includes a deflecting portion within the lumen proximal to the side port of the dilator, the deflecting portion having a surface that guides a guidewire laterally from a central axis of the lumen through the side port of the dilator and into the aligned side port of the vascular sheath.

4. The assembly of claim 3, wherein the deflecting portion of the dilator is characterized by a gradually sloping, smooth surface allowing the guidewire to glide toward the side port of the dilator.

5. The assembly of claim 1, wherein a first marker is included on the proximal end of the vascular sheath and a second marker is included on the proximal end of the dilator, wherein:
the second visual marker on the dilator is positioned to align with the first visual marker on the vascular sheath when the dilator is positioned within the vascular sheath, thereby ensuring accurate alignment of the side ports.

6. The assembly of claim 5, wherein the first marker and the second marker are selected from the group consisting of visual markers, tactile markers, and mechanical markers, wherein the mechanical markers include corresponding indentations or protrusions that allow the dilator to be inserted into the vascular sheath by fitting the mechanical features together to ensure alignment of the side ports.

7. The assembly of claim 1, wherein the side ports are aligned such that the guidewire is directed laterally from the lumen of the dilator through the side port and into the side port of the vascular sheath, facilitating access to a side vessel branching from a main vessel.

8. The assembly of claim 1, wherein the side port of the vascular sheath and the side port of the dilator are configured to facilitate positioning of the guidewire into the side vessel.

9. The assembly of claim 1, wherein during vascular access of the side vessel, the guidewire is advanced through the dilator until the guidewire engages a deflecting portion within the lumen of the dilator, wherein the deflecting portion is characterized by a gradually sloping, smooth surface, thereby allowing the guidewire to glide smoothly toward the side port of the dilator.

10. The assembly of claim 1, wherein the closed distal end of the dilator prevents the guidewire from exiting the distal tip, ensuring accurate guidewire placement.

11. A vascular sheath and dilator assembly comprising:
a vascular sheath including:
a tubular structure with a proximal end, a distal end, and a lumen extending longitudinally between the ends;
a side port located on a side of the tubular structure and extending into the lumen of the tubular structure;
a first marker positioned on the proximal end aligned with the side port;
a dilator configured for insertion into the lumen of the vascular sheath, the dilator including:
a cylindrical structure with a proximal end, a distal end, and a lumen extending longitudinally between the ends;
a side port on a side of the cylindrical structure extending into the lumen of the cylindrical structure and aligned with the side port of the vascular sheath when the dilator is fully inserted into the vascular sheath;
a second marker on the proximal end of the dilator aligned with the side port of the dilator;
wherein, vascular access into a side vessel branching off a main vessel using the vascular sheath and dilator assembly comprises:
inserting the vascular sheath into a vascular vessel and aligning the side port of the vascular sheath with a side vessel branching from a main vessel;
inserting the dilator into the lumen of the vascular sheath and aligning the side port of the dilator with the side port of the vascular sheath;
advancing a guidewire through the lumen of the dilator; and
guiding the guidewire laterally through the side port of the dilator and into the aligned side port of the vascular sheath, thereby directing the guidewire into a side vessel branching from a main vessel.

12. The assembly of claim 11, wherein the second marker on the dilator is aligned with the first marker on the vascular sheath to ensure accurate alignment of the side ports of the dilator and the vascular sheath when the dilator is inserted into the vascular sheath.

13. The assembly of claim 11, wherein the first marker and the second marker are selected from the group consisting of visual markers, tactile markers, and mechanical markers, wherein the mechanical markers include corresponding indentations or protrusions that allow the dilator to be inserted into the vascular sheath by fitting the mechanical features together to ensure alignment of the side ports.

14. The assembly of claim 11, wherein the dilator further includes a deflecting portion within the lumen proximal to the side port of the dilator, the deflecting portion having a surface that guides a guidewire laterally from a central axis of the lumen through the side port of the dilator and into the aligned side port of the vascular sheath.

15. The assembly of claim 14, wherein the deflecting portion of the dilator is characterized by a gradually sloping, smooth surface allowing the guidewire to glide smoothly toward the side port on the dilator.

16. The assembly of claim 11, wherein the side port on the dilator and the side port on the vascular sheath are aligned such that a guidewire is directed laterally from the lumen of the dilator through the side port of the dilator and into the side port of the vascular sheath, facilitating access to a side vessel branching from a main vessel.

17. The assembly of claim 11, wherein during the vascular access of the side vessel the guidewire is advanced through the dilator until the guidewire engages a deflecting portion within the lumen of the dilator, wherein the deflecting portion is characterized by a gradually sloping, smooth surface, thereby allowing the guidewire to glide smoothly toward the side port of the dilator.

18. The assembly of claim 11, wherein during the vascular access of the side vessel the alignment of the first and second markers on the proximal ends of the vascular sheath and the dilator ensures proper positioning of the side port of the dilator with the side port of the vascular sheath for accurate guidewire placement.

* * * * *